(12) United States Patent
Thorn et al.

(10) Patent No.: US 7,064,225 B2
(45) Date of Patent: Jun. 20, 2006

(54) SYNTHESIS OF ANSA-METALLOCENES AND THEIR PARENT LIGANDS IN HIGH YIELD

(75) Inventors: Matthew G. Thorn, Bartlesville, OK (US); Joel L. Martin, Bartlesville, OK (US); Qing Yang, Bartlesville, OK (US); Albert P. Masino, Tulsa, OK (US)

(73) Assignee: Chevron Phillips Chemical Company, L.P., The Woodlands, TX (US)

( * ) Notice: Subject to any disclaimer, the term of this patent is extended or adjusted under 35 U.S.C. 154(b) by 0 days.

(21) Appl. No.: 10/876,948

(22) Filed: Jun. 25, 2004

(65) Prior Publication Data

US 2005/0285284 A1 Dec. 29, 2005

(51) Int. Cl.
*C07F 17/00* (2006.01)
*C07C 2/50* (2006.01)

(52) U.S. Cl. ........................................ 556/53; 585/361
(58) Field of Classification Search ................. 556/53; 585/361
See application file for complete search history.

(56) References Cited

U.S. PATENT DOCUMENTS 5,225,500 A * 7/1993 Elder et al. .................. 526/127
5,498,581 A 3/1996 Welch et al.
5,565,592 A 10/1996 Patsidis et al.
6,509,427 B1 1/2003 Bruce et al.

OTHER PUBLICATIONS

Kajigaeshi, S. et al., Selective Preparation Of Fluorene Derivatives Using the t-Butyl Function As A Positional . . . , The Chem. Society of Japan, vol. 59, p. 97 (1986).
Alt, H.G. et al., Journal of Organometallic Chemistry vol. 562, pp. 153-181 (1998).
Alt, H.G. et al., Journal Of Organometallic Chemistry, vol. 568, pp. 87-112 (1998).
Koppl, A. et al., "Heterogeneous Metallocene Catalysts for Ethlene Polymerization", Journal of Molecular Catalysts A: Chemical, vol. 165, pp. 23-32 (2001).
International Search Report and Written Opinion, PCT/US05/022533, Dec. 2, 2005, 12 pages.
Ricardo Fierro, "Synthesis and characterization of new one-carbon-bridged titanocene and zirconocene derivatives", Journal of Organometallic Chemistry, vol. 485, No. 1, Jan. 11, 1995, pp. 11-17.

* cited by examiner

*Primary Examiner*—Porfirio Nazario-Gonzalez
(74) *Attorney, Agent, or Firm*—Womble Carlyle Sandridge & Rice, PLLC

(57) ABSTRACT

The present invention provides a method of making compounds comprising linked cyclopentadienyl and fluorenyl groups, including substituted analogs thereof, which are precursors to ansa-metallocenes comprising bridged cyclopentadienyl and fluorenyl ligands. In one aspect, this invention provides a preparative method for (5-cyclopentadienyl)[5-(2,7-di-tert-butylfluorenyl)]hex-1-ene, and ansa-metallocenes comprising this ligand.

67 Claims, 2 Drawing Sheets

SYNTHESIS OF ANSA-METALLOCENES AND THEIR PARENT LIGANDS IN HIGH YIELD

TECHNICAL FIELD OF THE INVENTION

This invention relates to the fields of organic synthesis and organometallic synthesis, including synthetic methods for ansa-metallocenes, and their parent ligands.

BACKGROUND OF THE INVENTION

Metallocene compounds constitute useful catalyst components for a variety of chemical transformations including olefin polymerizations, where metallocenes are often used in combination with a variety of cocatalysts. It is generally accepted that the metallocene structure itself is intimately involved in determining the physical properties of the resulting polyolefin and hence its eventual usefulness in a variety of end-use applications such as in film, pipe and blow-molded articles. Therefore, there is a need to develop new methods to prepare metallocenes that allow an assortment of substituents to be incorporated into the metallocene structure.

It is likewise of interest to develop new methods to prepare bridged or ansa-metallocene compounds, which comprise two $\eta^5$-cyclopentadienyl-type ligands linked by a chemical spacer. A variety of substituents can be incorporated into the ansa-metallocene structure, including substituents on the cyclopentadienyl-type ligands, on the bridging group, or both, each of which helps determine the physical properties of polyolefins prepared using these compounds. To accomplish this task, it is also of interest to develop new preparative methods for the ansa-metallocene parent ligand comprising two cyclopentadienyl-type groups linked by a bridging group.

SUMMARY OF THE INVENTION

This invention encompasses methods for the synthesis of organic compounds comprising two cyclopentadienyl-type groups linked by a bridging group, which constitute useful ligands in preparing ansa-metallocene complexes. These ansa-metallocenes can be used subsequently as catalyst components in olefin polymerizations. In one aspect, the methods of this invention generally afford higher yields of the desired product than were heretofore available. In one aspect, for example, the methods disclosed herein permit a range of substituents to be incorporated into the ligand and the ansa-metallocene, which in turn can affect and determine the physical properties of polyolefins prepared using these compounds.

In one aspect of this invention, a method is provided for the synthesis of compounds comprising linked cyclopentadienyl and fluorenyl groups, including substituted analogs thereof, which are precursors to ansa-metallocenes comprising bridged cyclopentadienyl and fluorenyl ligands. However, this method is also applicable to ligands comprising linked cyclopentadienyl and indenyl groups, indenyl and fluorenyl groups, two cyclopentadienyl groups, two indenyl groups, or two fluorenyl groups. This invention will be illustrated throughout by examples for the preparation of linked cyclopentadienyl and fluorenyl groups and ansa-metallocenes comprising bridged cyclopentadienyl and fluorenyl ligands. In this aspect, for example, this invention provides a new high-yield method for making the metallocene, (5-cyclopentadienyl)[5-(2,7-di-tert-butylfluorenyl)]hex-1-ene zirconium dichloride, as well as its parent ligand, (5-cyclopentadienyl)[5-(2,7-di-tert-butylfluorenyl)]hex-1-ene. However, many variations in the substitution patterns for this ligand and ansa-metallocene are possible, as disclosed herein.

In one aspect, this invention provides a method for making a compound of the formula

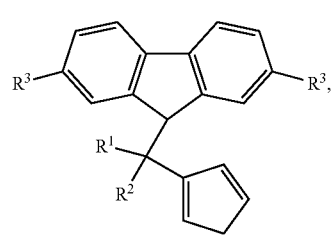

(I)

and isomers thereof, comprising:
a) contacting a compound of the formula

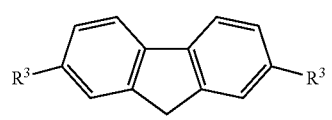

(II)

and an alkyl lithium reagent in an ethereal solvent to form a first mixture, wherein compound II is substantially deprotonated to form Li(II);

b) rapidly combining the first mixture with a fulvene compound of the formula

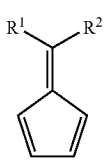

(III)

to form a second mixture, wherein either Li(II) or compound III is optionally a limiting reagent, and wherein the limiting reagent, if present, has substantially reacted; and c) contacting the second mixture with a proton source to form a third mixture comprising

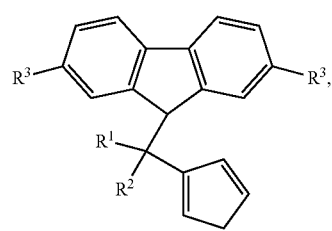

(I)

and isomers thereof;
wherein $R^1$ and $R^2$ independently are hydrogen or an aliphatic or substituted aliphatic group having from 1 to about 20 carbon atoms; and wherein each $R^3$ independently is hydrogen or an aliphatic or substituted aliphatic group having from 1 to about 20 carbon atoms.

Typically, compound I is formed in at least about 85% yield, at least about 90% yield, or at least about 95% yield.

For example, compounds of the formula I that can be prepared using this invention include the compound of the formula

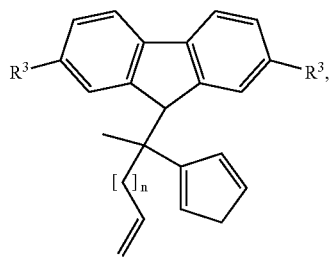

which can be prepared as disclosed herein using the precursors

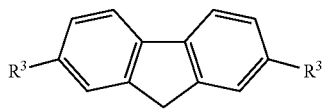
(II)

(II) and compound III having the formula

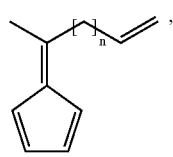

wherein $R^3$ can be typically H, t-butyl, i-propyl, n-propyl, ethyl, or methyl, and wherein n is an integer from 1 to about 6.

In another aspect, this invention provides a method of making a compound of the formula

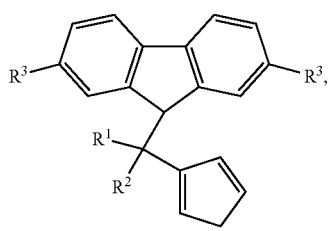
(I)

and isomers thereof, comprising:

a) providing a source of a fluorenyl anion having the formula

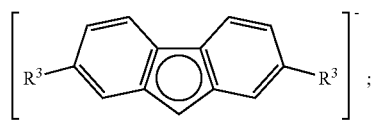

b) rapidly combining the source of the fluorenyl anion with a fulvene compound of the formula

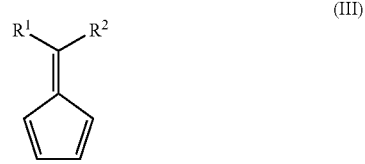
(III)

to form a mixture, wherein either the source of the fluorenyl anion or compound III is optionally a limiting reagent, and wherein the limiting reagent, if present, has substantially reacted; and c) contacting the mixture with a proton source to form

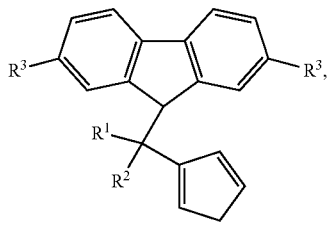
(I)

and isomers thereof;

wherein $R^1$ and $R^2$ independently are hydrogen or an aliphatic or substituted aliphatic group having from 1 to about 20 carbon atoms; and wherein each $R^3$ independently is hydrogen or an aliphatic or substituted aliphatic group having from 1 to about 20 carbon atoms.

In this aspect, for example, the source of the fluorenyl anion having the formula

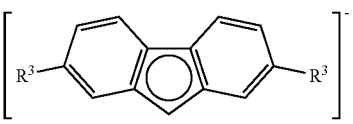

can typically comprise lithium, sodium, potassium, magnesium, calcium, or a combination thereof, in addition to comprising the fluorenyl anion. For example, the source of the fluorenyl anion having the formula

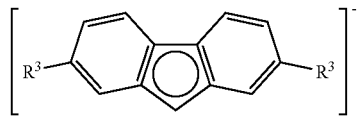

can typically comprise a salt of the fluorenyl anion comprising lithium, sodium, potassium, magnesium, calcium, or a combination thereof.

The ethereal solvent used in this method, can be independently selected from a range of ethereal solvents, including, but not limited to, dimethyl ether, diethyl ether, diisopropyl ether, di-n-propyl ether, di-n-butyl ether, methyl t-butyl ether, diphenyl ether, THF, 1,2-dimethoxyethane, or any combination thereof.

In another aspect of the invention, the rapid combination of the ethereal solution of the fluorenyl component Li(II) and the fulvene compound III, is typically carried out over a time period of less than about 1 minute. This combination time for the fluorenyl and the fulvene compounds is different than the total contact time between these compounds, prior to proceeding to the subsequent step in the process. The combination time describes the elapsed time over which the addition of the fulvene to the ethereal solution of the fluorenyl, or alternatively, the addition of the ethereal solution of fluorene compound to the fulvene, is initiated and completed.

This method can further comprise isolating compound I. For example, the method of this invention can further comprise removing the volatile components from the third mixture to provide a residue comprising I, optionally triturating the residue with a solvent in which I is substantially insoluble and III is soluble, and isolating I. Examples of solvents that are useful in this trituration include, but are not limited to, alcohols having up to about 8 carbon atoms, examples of which include, but are not limited to methanol, ethanol, i-propanol, n-propanol, n-butanol, sec-butanol, t-butanol, 1-hexanol, 2-hexanol, 3-hexanol, any mixture thereof, or any combination thereof.

In a further aspect of this invention, a method is provided for making an ansa-metallocene compound of the formula

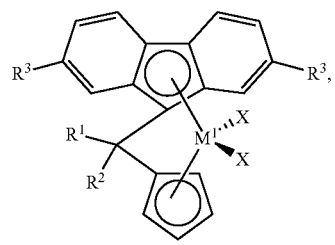

comprising:

a) contacting a compound of the formula

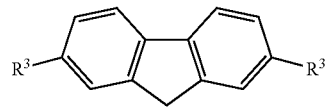

and a first alkyl lithium reagent in a first ethereal solvent to form a first mixture, wherein compound II is substantially deprotonated to form Li(II);

b) rapidly combining the first mixture with a fulvene compound of the formula

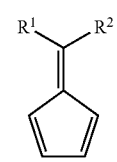

to form a second mixture, wherein the limiting reagent has substantially reacted;

c) contacting the second mixture with a proton source to form a third mixture comprising

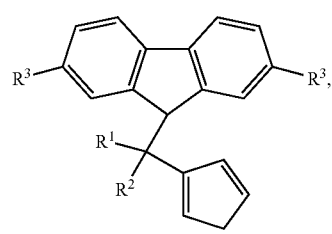

including isomers thereof, in at least about 85% yield;

d) removing the volatile components from the third mixture to provide a residue comprising I;

e) optionally triturating the residue with a solvent in which I is substantially insoluble and III is soluble to provide I, followed by isolation of I;

f) contacting the I with from about 2 to about 2.5 molar equivalents of a second alkyl lithium reagent in a second ethereal solvent to form a fourth mixture, wherein the I is substantially deprotonated to form $Li_2(I)$;

g) contacting the fourth mixture with $M^1X_4$ and an optional hydrocarbon cosolvent to form a fifth mixture comprising

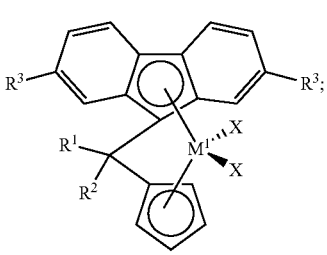

h) removing the volatile components from the fifth mixture to provide IV in at least about 80% yield;

i) optionally washing the IV in a non-polar solvent;

j) optionally extracting the IV with a polar solvent followed by removing the volatiles from the polar solvent solution to provide IV; and k) optionally crystallizing the IV from an aromatic solvent;

wherein:

$R^1$ and $R^2$ are independently selected from an aliphatic or substituted aliphatic group having from 1 to about 20 carbon atoms, or hydrogen; and $R^3$, in each instance, is independently selected from an aliphatic or substituted aliphatic group having from 1 to about 20 carbon atoms, or hydrogen;

$M^1$ is Zr or Hf; and

X is Cl, Br, or I.

It was found that yields of the metallocene were improved when the volatile components were removed from the fifth mixture to provide IV.

This method can also be used to prepare a zirconocene analog having the structure

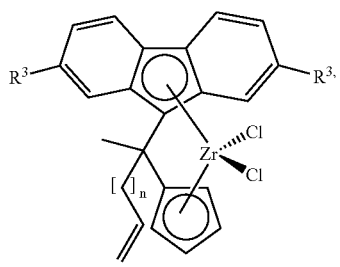

(IV)

according to the method disclosed herein, wherein compound I has the formula

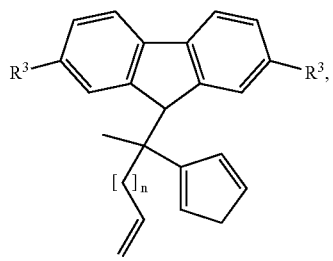

compound II has the formula

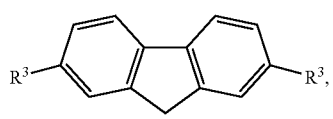

and compound III has the formula

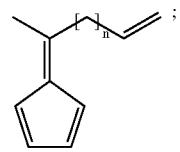

wherein:

$R^3$ is H, t-butyl, i-propyl, n-propyl, ethyl, or methyl; and n is an integer from 1 to about 6.

As disclosed herein for the parent ligand, in this aspect also, the rapid combination of a fluorenyl component Li(II) with a fulvene component III is typically carried out over a time period of less than about 5 minutes, less than about 3 minutes, less than about 1 minute, or less than about 15 seconds. This combination time for the fluorenyl and the fulvene compounds is different than the total contact time between these compounds, prior to proceeding to the subsequent step in the process.

Also in this aspect, the first and second ethereal solvents used in the preparation of the metallocene can be independently selected from a range of ethereal solvents, including, but not limited to, dimethyl ether, diethyl ether, diisopropyl ether, di-n-propyl ether, di-n-butyl ether, methyl t-butyl ether, diphenyl ether, THF, 1,2-dimethoxyethane, or any combination thereof.

This method of preparing the metallocene, which comprises removing the volatile components from the third mixture to provide a residue comprising I, can also optionally comprise triturating the residue with a solvent in which I is substantially insoluble and III is soluble to provide I, followed by isolation of I. Examples of solvents that are useful in this trituration include, but are not limited to, alcohols having up to about 8 carbon atoms, examples of which include, but are not limited to, methanol, ethanol, i-propanol, n-propanol, n-butanol, sec-butanol, t-butanol, 1-hexanol, 2-hexanol, 3-hexanol, any mixture thereof, or any combination thereof.

These and other aspects, features, embodiments, and advantages of the present invention will become apparent after a review of the following detailed description of the disclosed features.

The following patent applications, filed contemporaneously with the present application, are incorporated by reference herein in their entireties: U.S. patent application Ser. No. 10/877,039 U.S. patent application Ser. No. 10/876,891 U.S. patent application Ser. No. 10/876,930 and U.S. patent application Ser. No. 10/877,021.

BRIEF DESCRIPTION OF THE FIGURES

The following is a brief description of the Figures.

DETAILED DESCRIPTION OF THE INVENTION

Figure 1:
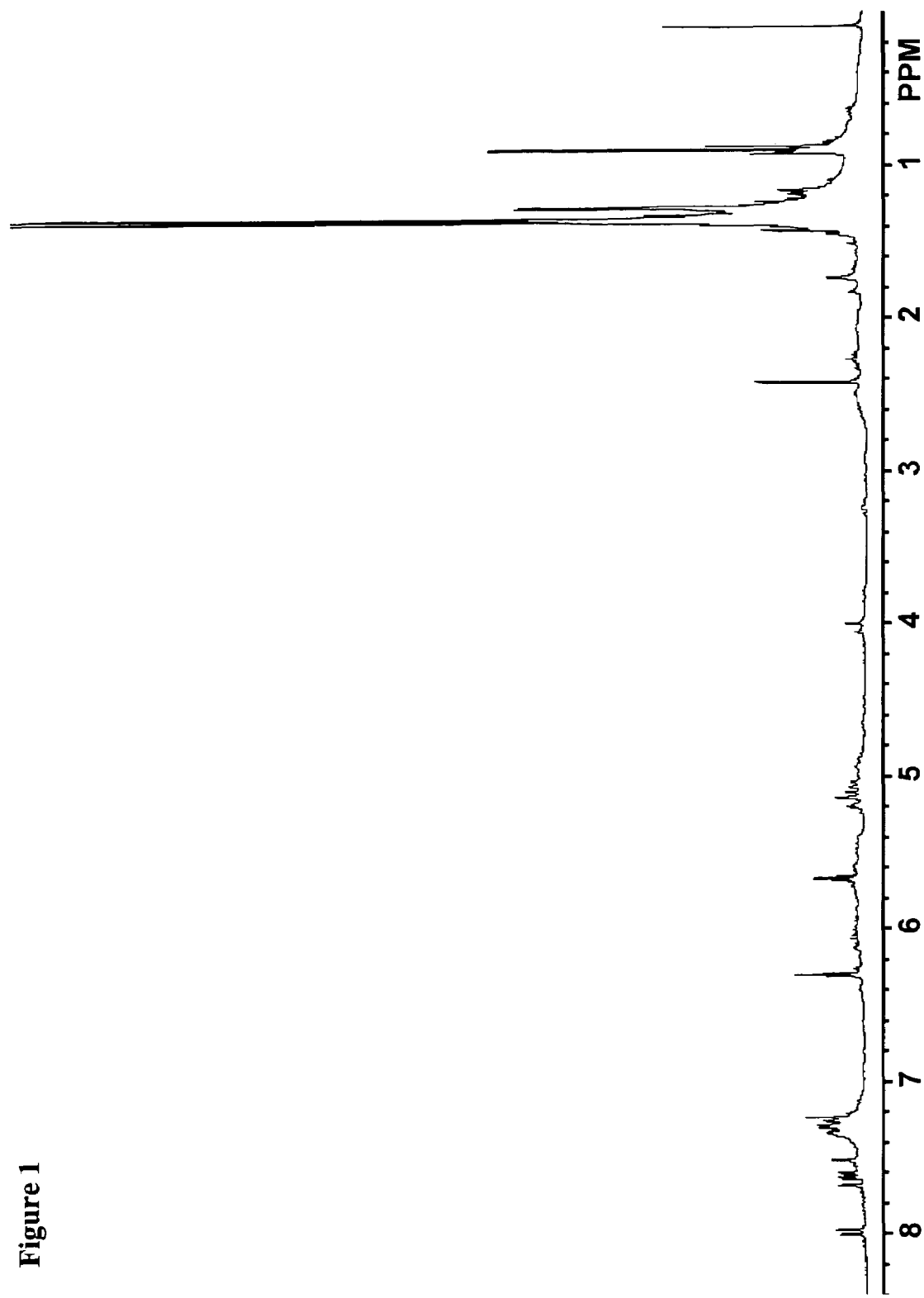
FIG. 1 represents a $^1$H NMR spectrum in CDCl$_3$ of the pentane washing step, after removal of the volatiles, for the synthesis of (5-cyclopentadienyl)[5-(2,7-di-tert-butylfluorenyl)]hex-1-ene zirconium dichloride.

The present invention provides a method of making a variety of organic compounds comprising two cyclopentadienyl-type groups linked by a bridging group, which constitute useful ligands in preparing ansa-metallocene complexes. The methods disclosed herein can be applied to the preparation of compounds comprising linked cyclopentadienyl and fluorenyl groups, linked cyclopentadienyl and indenyl groups, linked indenyl and fluorenyl groups, two linked cyclopentadienyl groups, two linked indenyl groups, two linked fluorenyl groups. In each case, these compounds can serve as precursor ligands to the corresponding ansa-metallocenes, which themselves can be used as catalyst components in olefin polymerizations. In one aspect, the methods of this invention generally afford higher yields of the desired product than were heretofore available.

Ligand Synthesis. In one aspect, the present invention provides a method for making a compound of the formula

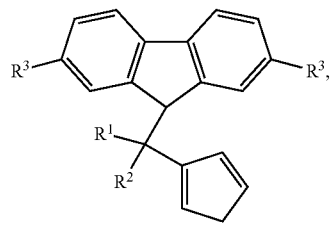

including isomers thereof, in at least about 85% yield, comprising:

a) contacting a compound of the formula

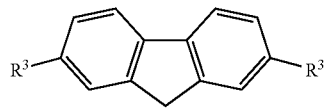

and an alkyl lithium reagent in an ethereal solvent to form a first mixture, wherein compound II is substantially deprotonated to form Li(II);

b) rapidly combining the first mixture with a fulvene compound of the formula

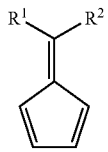

to form a second mixture, wherein the limiting reagent has substantially reacted; and c) contacting the second mixture with a proton source to form a third mixture comprising

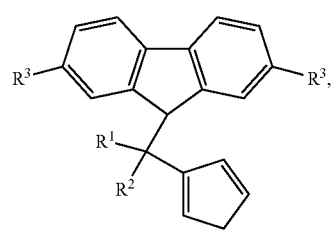

including isomers thereof;

wherein:

$R^1$ and $R^2$ are independently selected from an aliphatic or substituted aliphatic group having from 1 to about 20 carbon atoms, or hydrogen; and $R^3$, in each instance, is independently selected from an aliphatic or substituted aliphatic group having from 1 to about 20 carbon atoms, or hydrogen.

This method provides I in at least about 85% yield, at least about 90% yield, or at least about 95% yield.

In the formulas I, II, and III, $R^1$ and $R^2$ can be independently selected from an aliphatic or substituted aliphatic group having from 1 to about 20 carbon atoms, or hydrogen; and $R^3$, in each instance, is independently selected from an aliphatic or substituted aliphatic group having from 1 to about 20 carbon atoms, or hydrogen. Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having from one to about 20 carbon atoms. Thus, aliphatic groups include, but are not limited to, hydrocarbyls such as paraffins and alkenyls. For example, aliphatic groups as used herein include methyl, ethyl, propyl, n-butyl, tert-butyl, sec-butyl, isobutyl, amyl, isoamyl, hexyl, cyclohexyl, heptyl, octyl, nonyl, decyl, dodecyl, 2-ethylhexyl, pentenyl, butenyl, and the like.

The term isomers thereof, when used to describe the compound of formula I, is generally used to indicate that this method can provide enantiomers or diastereomers which can arise depending upon the identity of $R^1$, $R^2$, and each $R^3$ moiety, all of which are independently selected, and this method can also provide regioisomers resulting from where the bridging group bonds to the cyclopentadienyl ring. The regioisomers of I would likely arise as a result of the regiochemistry of protonating the anionic complex formed from the reaction of Li(II) with III.

In another aspect, this method for making the ligand I comprises contacting a compound of the formula II and an alkyl lithium reagent in an ethereal solvent to form a first mixture, wherein compound II is substantially deprotonated to form Li(II). In this aspect, this deprotonation reaction can by typically carried out with an equimolar amount of II and an alkyl lithium reagent, or with a slight excess of either, but is typically carried out with from about 1.1 to about 1.2 molar equivalents of alkyl lithium reagent so that compound II is substantially deprotonated to form Li(II). In this aspect, the alkyl lithium reagent that can be used is any alkyl lithium reagent that allows I to be prepared in at least about 85% yield, including, but not limited to MeLi, n-BuLi, t-BuLi, n-hexylLi, LiCH$_2$SiMe$_3$, LiCH$_2$Ph, LiCH$_2$CMe$_3$, or any combination thereof. Therefore, the II and the alkyl lithium reagent react to form Li(II) in at least about 85% yield to be substantially deprotonated, however, typically, II and the alkyl lithium reagent react to form Li(II) in at least about 90% yield, at least about 95% yield, or at least about 98% yield. While other reagents may be used to deprotonate II, the lithium alkyls, including n-BuLi, work well in this synthetic method. Thus, in this aspect, the duration of the contact time between II and an alkyl lithium reagent is typically that time necessary to substantially deprotonate II, that is the time necessary to form Li(II) in at least about 85% yield, at least about 90% yield, at least about 95% yield, or at least about 98% yield The ethereal solvent used in this method, can be independently selected from a range of ethereal solvents, including, but not limited to, dimethyl ether, diethyl ether, diisopropyl ether, di-n-propyl ether, di-n-butyl ether, methyl t-butyl ether, diphenyl ether, THF, 1,2-dimethoxyethane, or any combination thereof. In one aspect, the ethereal solvent can be diethyl ether, THF, or any combination thereof, and in another aspect, the ethereal solvent can comprise diethyl ether.

In another aspect of the invention, the rapid combination of a fluorenyl compound Li(II) with a fulvene compound III is typically carried out over a time period of less than about 5 minutes, less than about 4 minutes, less than about 3 minutes, less than about 2 minutes, less than about 1 minute, less than about 45 seconds, less than about 30 seconds, or less than about 15 seconds. In this aspect, the rapid combination of Li(II) with III can also be carried out over a time period of less than about 1 minute, less than about 50 seconds, less than about 40 seconds, less than about 30 seconds, less than about 20 seconds, or less than about 10 seconds. This combination time for the fluorenyl and the fulvene compounds is different than the total contact time between these compounds, prior to proceeding to the subsequent step in the process. The combination time describes the elapsed time over which the addition of the fulvene to the ethereal solution of the fluorenyl, or alternatively, the addition of the ethereal solution of fluorene compound to the fulvene, is initiated and completed.

While not intending to be bound by theory, one explanation of why the rapid combination of the fulvene and the ethereal solution of the lithium fluorenyl results in high yields is as follows. It is possible that an intermediate, mono-lithiated species, namely Li(I), forms relatively quickly upon reacting Li(II) with III. Again, while not intending to be bound by theory, it is also possible that Li(II) could engage in a slower deprotonation reaction of Li(I) to form Li$_2$(I), along with fluorene. In this situation, slow combination of III to Li(II) might be expected to allow rapidly-formed Li(I) to be present together in solution with unreacted Li(II) for a sufficient period of time for the Li(II) to deprotonate Li(I) to form Li$_2$(I). This process would, in turn, be expected to lower the yield of Li(I) and its product I that would form upon quenching this reaction mixture with a proton source. In contrast, and again while not intending to be bound by theory, the rapid combination of III and Li(II) might be expected to form Li(I) quickly and deplete the Li(II) before it could engage in the slower reaction with Li(I) to the extent necessary to reduce the yield of I.

Still another aspect of this invention is the combination of the ethereal solution of Li(II) and III, which is typically carried out using from about a 1:1 molar ratio to about a 1:1.5 molar ratio of Li(II):III. This preparative method works with an excess of either reagent, but also works well using about a 1:1 molar ratio of these reagents. In the event there is an excess of one reagent over the other, the limiting reagent in this reaction can be present in at least about 50% the mole fraction of the non-limiting reagent, at least about 75% the mole fraction of the non-limiting reagent, or at least about 90% the mole fraction of the non-limiting reagent. Also in the aspect, in the combination of the ethereal solution of Li(II) and III, typically III is present in slight excess over Li(II).

In yet another aspect of the present invention, the concentration of the Li(II) compound in the first mixture, prior to rapidly combining this ethereal Li(II) solution with the fulvene compound III, can be from about 0.2 M (molar) to about 2.0 M. This Li(II) concentration in the first mixture, prior to rapidly combining this mixture with III, can also be from about 0.5 M to about 1.8 M, from about 0.7 M to about 1.5 M, or from about 1.0 M to about 1.2 M. Further, this Li(II) concentration in the first mixture, prior to rapidly combining this mixture with III, can also be about 0.5 M, about 0.6 M, about 0.7 M, about 0.8 M, about 0.9 M, about 1.0 M, about 1.1 M, about 1.2 M, about 1.3 M, about 1.4 M, about 1.5 M, about 1.6 M, about 1.7 M, about 1.8 M, about 1.9 M, or about 2.0 M.

Because the method of making I provides this compound in at least about 85% yield, the preparative method, in the event there is an excess of one reagent over the other in the combination of the ethereal solution of Li(II) and III, at least about 85% of the limiting reagent reacts, at least about 90% of the limiting reagent reacts, or at least about 95% of the limiting reagent reacts. Thus, in this aspect, the duration of the contact time between Li(II) and III is typically that time necessary such that the limiting reagent has substantially reacted, that is the time necessary for at least about 85% of the limiting reagent to be consumed, at least about 90% of the limiting reagent be consumed, or at least about 95% of the limiting reagent be consumed.

In another aspect, this invention encompasses contacting the second mixture, formed from rapidly combining the ethereal solution of Li(II) with III, with a proton source to form a third mixture comprising I. The proton source for this step can be any proton source that protonates the Li(II) with III contact product to provide I. In this aspect, the proton source can comprise water, an aqueous acid, an aqueous ammonium salt, or any combination thereof. The proton source can also be water, an aqueous acid, an aqueous ammonium salt, or any combination thereof. While not required, when the proton source comprises or is an aqueous acid, the aqueous acid can be relatively dilute, for example, from about 0.5 M to about 4 M. Typically, the proton source comprises an aqueous ammonium salt.

This method for making compound I can further comprise isolating compound I. Compound I can typically be isolated in at least about 85% yield. For example, the method of this invention can further comprise removing the volatile components from the third mixture to provide a residue comprising I, optionally contacting or triturating the residue with a solvent in which I is substantially insoluble and III is soluble, and isolating I. Thus, by describing the trituration solvent as a solvent in which I is substantially insoluble and III is soluble, it is intended that this solvent would provide for the isolation of I in the yields disclosed herein.

Examples of solvents that are useful in this trituration include, but are not limited to, an alcohol, including, but not limited to an alcohol having up to about 8 carbon atoms. Examples of trituration solvents that can be used in this aspect of the invention include, but are not limited to, methanol, ethanol, i-propanol, n-propanol, n-butanol, sec-butanol, t-butanol, 1-hexanol, 2-hexanol, 3-hexanol, any mixture thereof, or any combination thereof. Typically, the trituration solvent can comprise methanol, ethanol, any mixture thereof, or any combination thereof. In this aspect, removing the volatile components of the third mixture can be achieved by any method known to one of ordinary skill in the art, including, but not limited to, evaporation, evaporation under reduced pressure, evaporation under the flow of a gas such as nitrogen, and the like. Similarly, isolating I following the optional trituration of the residue obtained upon removing the volatile components from the third mixture can be carried out by any method known to one of ordinary skill in the art, including, but not limited to, decanting the trituration solvent from the solid I, filtering off solid I, and the like.

Yet another aspect of this invention is the temperature at which the various contact steps are initiated, and the temperature at which the various contact steps are allowed to proceed or run for their duration. These two temperatures can be different or they can be the same. In one aspect, the initiation temperature for a contact step is different than the run temperature. Thus, contacting II and an alkyl lithium reagent in an ethereal solvent to form a first mixture, can typically be initiated from about room temperature to about −100° C., from about 0° C. to about −100° C., from about −30° C. to about −95° C., or from about −50° C. to about −90° C., or from about −70° C. to about −85° C. In another aspect, contacting II and an alkyl lithium reagent in an ethereal solvent to form a first mixture, can typically be initiated at about room temperature, at about 0° C., at about −20° C., at about −40° C., or at about −78° C. Once II and the alkyl lithium reagent have been contacted in an ethereal solvent to form a first mixture at the contact temperature, the first mixture can be maintained at one or more run temperatures for the duration of the contact step. In this aspect, for example, the run temperature can be from about room temperature to about −100° C., from about 0° C. to about −100° C., from about −30° C. to about −95° C., or from about −50° C. to about −90° C., or from about −70° C. to about −85° C. In another aspect, this run temperature can be at about room temperature, at about 0° C., at about −20° C., at about −40° C., or at about −78° C.

In another aspect, rapidly combining the ethereal solution of Li(II) with a fulvene compound III to form a second mixture, can typically be performed from about room temperature to about −100° C., from about 0° C. to about −100° C., from about −30° C. to about −95° C., or from about −50° C. to about −90° C., or from about −70° C. to about −85° C. The temperature at which this rapid combination occurs is the temperature at which the contact between Li(II) and III is initiated. Once initiated, the run temperature can be, for example, from about room temperature to about −100° C., from about 0° C. to about −100° C., from about −30° C. to about −95° C., or from about −50° C. to about −90° C., or from about −70° C. to about −85° C. In another aspect, this run temperature can be at about −78° C.

Compounds of the formula I that can be prepared using this invention include, but are not limited to, a compound of the formula

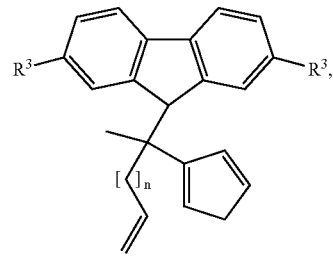

which can be prepared as disclosed herein by reacting the compound

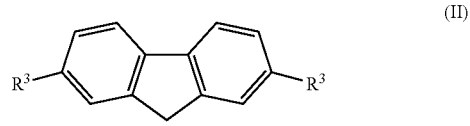

(II)

with a compound having the formula

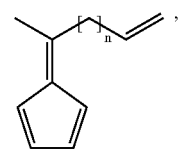

wherein $R^3$ can be typically H, t-butyl, i-propyl, n-propyl, ethyl, or methyl, and wherein n is an integer from 1 to about 6. In another aspect, $R^3$ can be typically t-butyl, i-propyl, n-propyl, ethyl, or methyl, and wherein n can be an integer from 1 to about 6.

Another compound of the formula I that can be prepared using this invention includes, but is not limited to, (5-cyclopentadienyl)[5-(2,7-di-tert-butylfluorenyl)]hex-1-ene. Thus, this invention provides a method for making (5-cyclopentadienyl)[5-(2,7-di-tert-butylfluorenyl)]hex-1-ene, comprising:

a) contacting 2,7-di-tert-butylfluorene and an alkyl lithium reagent in an ethereal solvent to form a first mixture, wherein the 2,7-di-tert-butylfluorene is substantially deprotonated to form Li(2,7-di-tert-butylfluorenyl);

b) rapidly combining the ethereal solution of Li(2,7-di-tert-butylfluorenyl) with 6-methyl-6-(3-butenyl)fulvene,

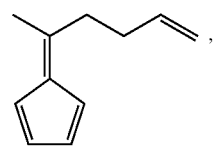

to form a second mixture, wherein the limiting reagent has substantially reacted; and c) contacting the second mixture with a proton source to form a third mixture comprising (5-cyclopentadienyl)[5-(2,7-di-tert-butylfluorenyl)]hex-1-ene in at least about 85% yield.

In another aspect of this invention, the method disclosed herein can further comprise isolating the (5-cyclopentadienyl)[5-(2,7-di-tert-butylfluorenyl)]hex-1-ene. This method can also further comprise removing the volatile components from the third mixture to provide a residue comprising (5-cyclopentadienyl)[5-(2,7-di-tert-butylfluorenyl)]hex-1-ene. In this aspect, this invention can also further comprise removing the volatile components from the third mixture to provide a residue comprising (5-cyclopentadienyl)[5-(2,7-di-tert-butylfluorenyl)]hex-1-ene, optionally triturating the residue with a solvent in which (5-cyclopentadienyl)[5-(2,7-di-tert-butylfluorenyl)]hex-1-ene is substantially insoluble and 6-methyl-6-(3-butenyl)fulvene is soluble, and isolating the (5-cyclopentadienyl)[5-(2,7-di-tert-butylfluorenyl)]hex-1-ene. Also in this aspect, this invention can further comprise isolating (5-cyclopentadienyl)[5-(2,7-di-tert-butylfluorenyl)]hex-1-ene in at least about 85% yield.

Scheme 1 illustrates one aspect of this invention for the synthesis of the parent ligand, in which typical conditions are exemplified. As shown in Scheme 1, about 1.1 to about 1.2 molar equivalents of n-butyl lithium were added to 2,7-di-tert-butylfluorene (V) in diethyl ether at −78° C., then this mixture was allowed to warm to room temperature and was stirred for at least about 12 hours. The reaction mixture was then cooled to −78° C. and 1.4 molar equivalents 6-butenyl-6-methylfulvene (VI) were added to the reaction mixture as quickly as possible, typically in less than about 1 minute. While not intending to be bound by theory, it is believed that this rapid addition helped to boost the yield of the parent ligand. This reaction mixture was then typically allowed to warm to room temperature, and was stirred for at least about 12 hours.

The Li(V) and VI reaction was then quenched using methods known in the art and the product was isolated as a crude white solid comprising VII. Further purification of the resulting parent ligand VII was then achieved through the use of a methanol wash, which afforded the parent ligand of a sufficiently high purity to be used in the subsequent metallocene synthesis. Using an alcohol wash, typically a methanol wash, rather than recrystallization, also helped boost the yield of the product.

If shorter reaction times were used, if pentane/Et$_2$O solvent mixtures of varying ratios were used for purification through crystallization of the crude ligand, or both, a reduction in the overall yield of the desired product was observed. The Examples provided herein disclose full details of the synthetic methods employed, and illustrate comparative preparations that provided the desired compound in lower yield.

Ansa-Metallocene Synthesis. In another aspect, the present invention provides a method for making a compound of the formula.

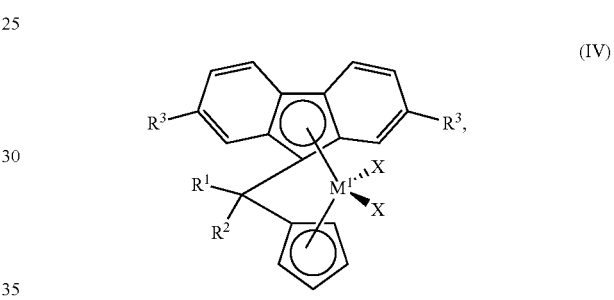

(IV)

comprising:

a) contacting a compound of the formula

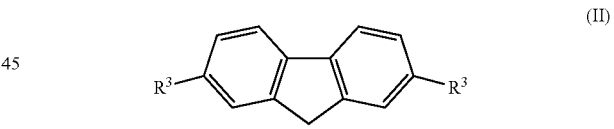

(II)

and a first alkyl lithium reagent in a first ethereal solvent to form a first mixture, wherein compound II is substantially deprotonated to form Li(II);

b) rapidly combining the first mixture with a fulvene compound of the formula

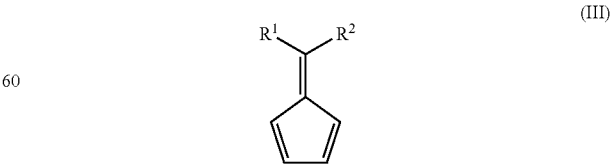

(III)

to form a second mixture, wherein the limiting reagent has substantially reacted;

Scheme 1

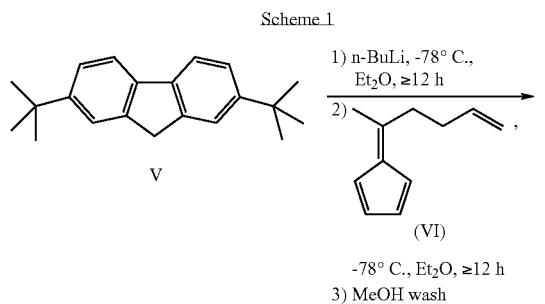

c) contacting the second mixture with a proton source to form a third mixture comprising

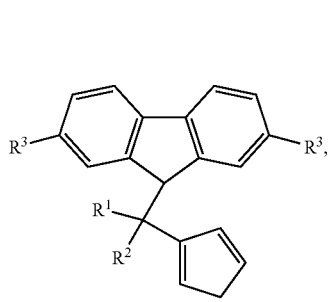
(I)

including isomers thereof, in at least about 85% yield;

d) removing the volatile components from the third mixture to provide a residue comprising I;

e) optionally triturating the residue with a solvent in which I is substantially insoluble and III is soluble to provide I, followed by isolation of I;

f) contacting the I with from about 2 to about 2.5 molar equivalents of a second alkyl lithium reagent in a second ethereal solvent to form a fourth mixture, wherein the I is substantially deprotonated to form $Li_2(I)$;

g) contacting the fourth mixture with $M^1X_4$ and an optional hydrocarbon cosolvent to form a fifth mixture comprising

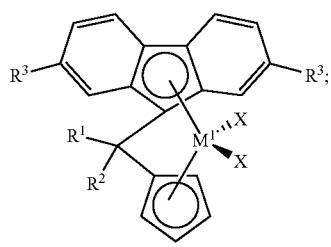
(IV)

h) removing the volatile components from the fifth mixture to provide IV in at least about 80% yield;

i) optionally washing the IV in a non-polar solvent;

j) optionally extracting the IV with a polar solvent followed by removing the volatiles from the polar solvent solution to provide IV; and k) optionally crystallizing the IV from an aromatic solvent; wherein:

$R^1$ and $R^2$ are independently selected from an aliphatic or substituted aliphatic group having from 1 to about 20 carbon atoms, or hydrogen; and $R^3$, in each instance, is independently selected from an aliphatic or substituted aliphatic group having from 1 to about 20 carbon atoms, or hydrogen;

$M^1$ is Zr or Hf; and

X is Cl, Br, or I.

In this aspect, compound I can have the formula

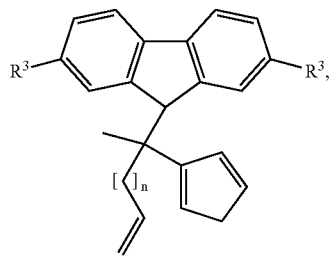

compound II can have the formula

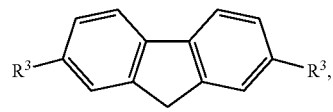

and compound III can have the formula

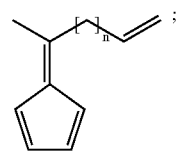

wherein:

$R^3$ is H, t-butyl, i-propyl, n-propyl, ethyl, or methyl, n is an integer from 1 to about 6;

$M^1$ is Zr; and

X is Cl.

Some of the preparative steps of this method encompass the preparation of the parent ligand that is used to prepare the ansa-metallocene in subsequent steps. Therefore, the various aspects disclosed herein for the preparation of the parent ligand are also applicable to that portion of the ansa-metallocene synthetic method that involved preparing the parent ligand, including but not limited to steps a, b, c, d and optional step e. Such aspects include, but are not limited to: contact time; solvents; combination time; initiation temperature; run temperature; alkyl lithium reagents; definitions of $R^1$, $R^2$, $R^3$, substantial deprotonation, substantial reaction, and limiting reagent; molar ratios; proton sources; yields; trituration solvents; method of isolation of I, and the like.

Also in this aspect, the first and the second alkyl lithium reagents are selected independently, that is independent of the selection of each other. Thus, the first alkyl lithium reagent that can be used is any alkyl lithium reagent that allows I to be prepared in at least about 85% yield, including, but not limited to MeLi, n-BuLi, t-BuLi, n-hexylLi, $LiCH_2SiMe_3$, $LiCH_2Ph$, $LiCH_2CMe_3$, or any combination thereof. The second alkyl lithium reagent that can be used is any alkyl lithium reagent that allows I to be deprotonated to form $Li_2(I)$ in at least about 85% yield, at least about 90% yield, at least about 95% yield, or at least about 98% yield. Thus, the second alkyl lithium reagent that can be used is any alkyl lithium reagent that allows IV to be prepared in at least about 85% yield, including, but not limited to MeLi, n-BuLi, t-BuLi, n-hexylLi, LiCH$_2$SiMe$_3$, LiCH$_2$Ph, LiCH$_2$CMe$_3$, or any combination thereof. While the first and the second alkyl lithium reagents are selected independently, n-BuLi is typically selected for the first alkyl lithium and the second alkyl lithium.

While not intending to be bound by theory, the contact time between I and the at least about 2 molar equivalents of a second alkyl lithium reagent is thought to affect the ansa-metallocene produced by this method. Accordingly, in this aspect, the contact time between I and the second alkyl lithium reagent can be at least about 0.5 hour, at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, or at least about 18 hours. Also in this aspect, the contact time between I and the second alkyl lithium reagent can be from about 1 hour to about 48 hours, from about 3 hours to about 30 hours, from about 6 hours to 24 hours, from about 8 hours to about 20 hours, or from about 10 hours to about 18 hours.

Similarly, the first and the second ethereal solvents are also selected independently, that is independent of the selection of each other. The first and second ethereal solvents used in this method, can be independently selected from a range of ethereal solvents, including, but not limited to, dimethyl ether, diethyl ether, diisopropyl ether, di-n-propyl ether, di-n-butyl ether, methyl t-butyl ether, diphenyl ether, THF, 1,2-dimethoxyethane, or any combination thereof. In one aspect, the first and second ethereal solvents can be independently selected from diethyl ether, THF, or any combination thereof, and in another aspect, the first and second ethereal solvents can independently comprise diethyl ether.

In another aspect of this invention, the optional hydrocarbon cosolvent can be a range of aliphatic and aromatic cosolvents, but can be typically an aliphatic cosolvent. In one aspect, the optional hydrocarbon cosolvent can be butane, pentane, cyclopentane, hexane, heptane, cyclohexane, methyl cyclopentane, octane, or any combination thereof. In this aspect, pentane can be a typical optional cosolvent.

The volatile components of the fifth mixture, like that of the third mixture, can be removed by any method known to one of ordinary skill in the art, including, but not limited to, evaporation, evaporation under reduced pressure, evaporation under the flow of a gas such as nitrogen, and the like.

Similarly, in still another aspect of this invention, the optional non-polar solvent that can be used to wash IV can be a range of non-polar solvents, including aliphatic or aromatic non-polar solvents. In this aspect, for example, the optional non-polar solvent can be butane, pentane, cyclopentane, hexane, heptane, cyclohexane, methyl cyclopentane, octane, or any combination thereof. Pentane can be a typical non-polar solvent used in this optional washing step of this invention.

Figure 2:
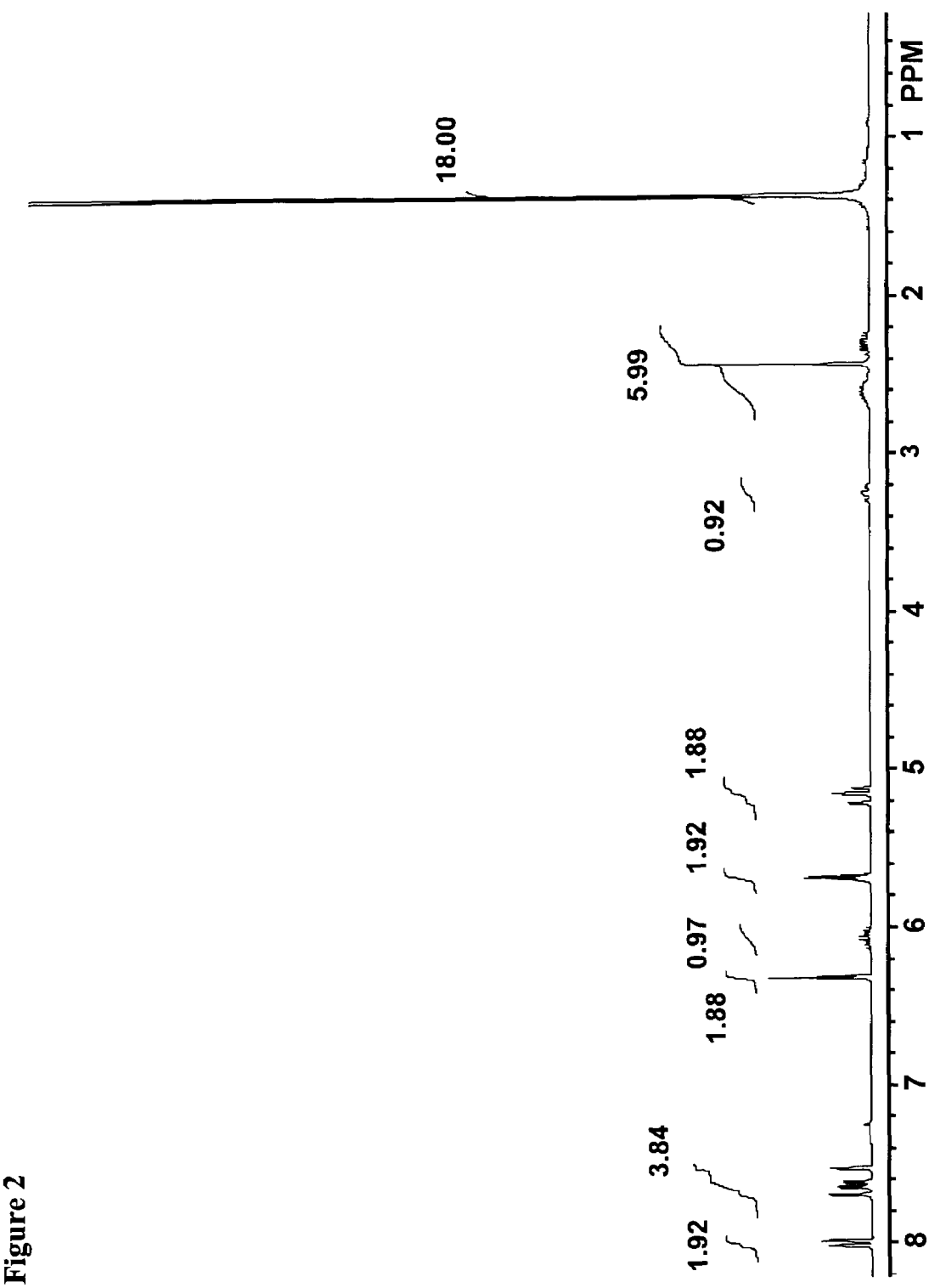
FIG. 2 represents a $^1$H NMR spectrum in CDCl$_3$ of the CH$_2$Cl$_2$ extract that followed after a pentane washing step, for the synthesis of (5-cyclopentadienyl)[5-(2,7-di-tert-butylfluorenyl)]hex-1-ene zirconium dichloride.

While not intending to be bound by theory, it is believed that the hydrocarbon, for example, pentane, wash functions primarily to improve the purity of the IV without sacrificing its yield, because the starting materials and by-products are soluble in solvents such as pentane, and IV is relatively insoluble (see FIGS. 1 and 2). If polar solvents such as ethereal solvents are used to wash the crude IV obtained after removing the reaction volatiles from the reaction mixture, the purity of IV is improved, but the yield of IV suffers because of its greater solubility in ethers as compared to pentane. Also while not intending to be bound by theory, it is believed that removing the reaction volatiles from the reaction mixture crude IV, rather than decanting the reaction solvent, helps improve the overall yield of IV, because of the solubility of IV in ethereal solvents.

In yet another aspect of this invention, the polar solvent that can be used to extract IV can be a range of polar solvents, including aliphatic or aromatic polar solvents. In this aspect, for example, the optional polar solvent can be CHCl$_3$, CH$_2$Cl$_2$, 1,2-dichlorethane, or any combination thereof. In this aspect, dichloromethane (CH$_2$Cl$_2$) is a typical polar solvent.

In a further aspect, the optional aromatic solvent that can be used to crystallize IV, can be a range of aromatic solvents, including, but not limited to, benzene, toluene, xylene, mesitylene, ethyl benzene, anisole, aniline, pyridine, 4-phenylpyridine, or any combination thereof, including any isomer thereof.

Scheme 2 illustrates one aspect of this invention for the synthesis of the ansa-metallocene VIII using the parent ligand VII prepared according to this invention, in which typical conditions are exemplified. As shown in Scheme 2, the process for preparing VIII in high yield encompassed using an appropriate length of time for deprotonation of VII, as well as the use of proper extraction procedures. For example, increasing the time for the deprotonation reaction of the parent ligand VII using n-butyl lithium from 6 hours to at least about 12 hours prior to addition to zirconium tetrachloride, increased the yield of metallocene VIII. Removing the volatile components of the Li$_2$(VII) and ZrCl$_4$ reaction mixture, rather than simply concentrating the solution and crystallizing out the metallocene VIII, afforded higher yields of VIII. Further, using pentane to wash the resulting residue or solid obtained from removing the reaction volatiles improved the purity of the desired product. Using a non-polar solvent such as pentane, rather than diethyl ether, to wash the resulting residue or solid obtained from removing the reaction volatiles improved the overall yield of the desired product.

Scheme 2

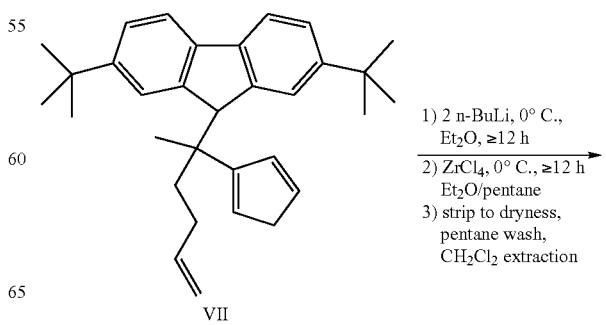

-continued

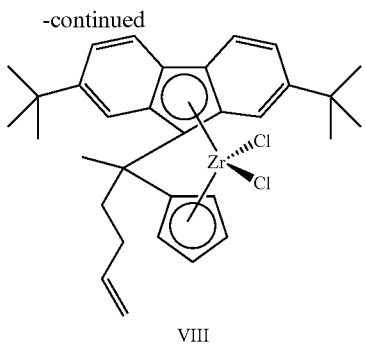

VIII

While metallocene VIII was somewhat soluble in nonpolar solvents such as pentane, it was more soluble in polar solvents such as $CH_2Cl_2$, which served as a suitable extraction solvent. FIG. 1 provides the $^1$H NMR spectrum in $CDCl_3$ solvent of the pentane extract, that is, the pentane wash liquid, used in the workup of the (5-cyclopentadienyl) [5-(2,7-di-tert-butylfluorenyl)]hex-1-ene zirconium dichloride synthesis. While some metallocene product can be observed in this spectrum, additional byproducts that were removed by this wash are also observed. FIG. 2 provides the $^1$H NMR spectrum in $CDCl_3$ solvent of the $CH_2Cl_2$ extract, that followed after a pentane washing step, from the solid product obtained during workup of the (5-cyclopentadienyl) [5-(2,7-di-tert-butylfluorenyl)]hex-1-ene zirconium dichloride synthesis. A high concentration of pure metallocene VIII is observed in this spectrum, illustrating the suitability of this method for preparing pure VIII, the suitability of pentane as a wash solvent to remove unwanted byproducts and unreacted starting material, and the suitability of $CH_2Cl_2$ as an extraction and crystallization solvent. The Examples provided herein disclose full details of the synthetic methods employed to provide the desired metallocene in high yield, and illustrate comparative preparations that provided the desired compound in lower yield.

In an additional aspect of this invention, the entire sequence of parent ligand synthesis and metallocene preparation could be performed in a "one-pot" process, and a representative procedure for this one-pot synthesis is provided in the Examples. Although the one-pot method allowed ansa-metallocene VIII to be prepared in sufficiently high purity for further use, including, but not limited to, its use in olefin polymerization catalysis, the overall yield of VIII was observed to be comparatively lower than that overall yield of VIII when the synthesis was conducted by first isolating the parent ligand VII.

Yet another aspect of this invention is the preparation of a compound of the formula

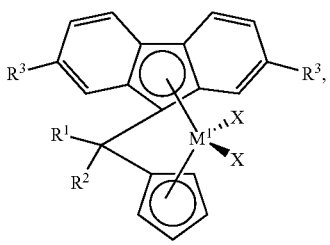

wherein $R^1$, $R^2$, $R^3$, $M^1$, and X are defined herein, using any process to prepare metallocene compounds that is know to one of ordinary skill, using the parent ligand prepared according to this invention. Thus, numerous processes to prepare metallocene compounds have been reported, examples of which include U.S. Pat. Nos. 4,939,217, 5,191, 132, 5,210,352, 5,347,026, 5,399,636, 5,401,817, 5,420,320, 5,436,305, 5,451,649, 5,496,781, 5,498,581, 5,541,272, 5,554,795, 5,563,284, 5,565,592, 5,571,880, 5,594,078, 5,631,203, 5,631,335, 5,654,454, 5,668,230, 5,705,579, and 6,509,427 which describe such methods, each of which is incorporated by reference herein, in its entirety. Other processes to prepare metallocene compounds that can be employed in this invention have been reported in references such as: Köppl, A. Alt, H. G. *J. Mol. Catal A.* 2001, 165, 23; Kajigaeshi, S.; Kadowaki, T.; Nishida, A.; Fujisaki, S. *The Chemical Society of Japan,* 1986, 59, 97; Alt, H. G.; Jung, M.; Kehr, G. *J. Organomet. Chem.* 1998, 562, 153–181; and Alt, H. G.; Jung, M. *J. Organomet. Chem.* 1998, 568, 87–112; each of which is incorporated by reference herein, in its entirety. Further, additional processes to prepare metallocene compounds that can be employed in this invention have been reported in: *Journal of Organometallic Chemistry,* 1996, 522, 39–54, which is incorporated by reference herein, in its entirety. The following treatises also describe such methods: Wailes, P. C.; Coutts, R. S. P.; Weigold, H. in Organometallic Chemistry of Titanium, Zirconium, and Hafnium, Academic; New York, 1974; Cardin, D. J.; Lappert, M. F.; and Raston, C. L.; Chemistry of Organo-Zirconium and -Hafnium Compounds; Halstead Press; New York, 1986; each of which is incorporated by reference herein, in its entirety.

For any particular compound disclosed herein, any general structure presented also encompasses all conformational isomers, regioisomers, and stereoisomers that may arise from a particular set of substituents. The general structure also encompasses all enantiomers, diastereomers, and other optical isomers whether in enantiomeric or racemic forms, as well as mixtures of stereoisomers, as the context requires.

EXAMPLES

The present invention is further illustrated by the following examples, which are not to be construed in any way as imposing limitations upon the scope thereof. On the contrary, it is to be clearly understood that resort may be had to various other aspects, features, embodiments, modifications, and equivalents thereof which, after reading the description herein, may suggest themselves to one of ordinary skill in the art without departing from the spirit of the present invention or the scope of the appended claims.

The following examples and comparative examples encompass new synthetic methods for both the ansa-metallocene parent ligands and for metallocenes prepared therefrom. Specifically, these examples demonstrate that product yields of an ansa-metallocene parent ligand can be improved by proper conditions for combining the ligand precursors. This invention is specifically illustrated using the two reactants, 2,7-di-tert-butylfluorenyl lithium and 6-butenyl-6-methylfulvene, and through the choice of the deprotonation method for the ligand precursor, selection of the reaction solvent, and selection of the reaction work-up conditions.

In addition, the following examples and comparative examples demonstrate that high product yields of an ansa-metallocene can be obtained by selection of the deprotonation conditions for the parent ligand, selection of the reaction solvent, and reaction work-up conditions, also as follows. Specifically, this aspect of the invention is illustrated in the preparation of the metallocene (5-cyclopentadienyl)[5-(2,7-di-tert-butylfluorenyl)]hex-1-ene zirconium dichloride.

General Details

The solvents used in the following Examples were dried and distilled under nitrogen using standard methods. The Nuclear Magnetic Resonance (NMR) spectra reported herein were obtained on a Varian Mercury Plus 300 NMR spectrometer operating at 300 MHz for $^1$H NMR (CDCl$_3$ solvent, referenced against the peak of residual CHCl$_3$ at 7.24 ppm).

The 6-butenyl-6-methylfulvene was prepared according to the method used by Stone and Little (*J. Org. Chem.* 1984, 49, 1849).

Example 1

Preparation of 1-(methyl)-1-(3-butenyl)-1-cyclopentadienyl)-1-(2,7-di-tert-butylfluorenyl)methane by the reaction of 2,7-di-tert-butylfluorenyl lithium and 6-butenyl-6-methylfulvene Preparation 1. A one-liter flask was charged with 2,7-di-tert-butylfluorene (50 g, 179.6 mmol) and a stir bar, capped with a rubber septum, and placed under a nitrogen atmosphere. Diethyl ether (about 200 mL) was added via a cannula, and the resulting mixture was cooled to –78° C. in a dry-ice bath. This mixture was stirred at this temperature as n-butyllithium (19.0 mL of 10 M in hexanes, 190 mmol) was added slowly via syringe. After the addition of n-butyllithium was complete, the reddish solution was slowly warmed to room temperature and stirred overnight (at least about 12 hours). After this time, the reaction mixture was cooled to –78° C., and 6-butenyl-6-methylfulvene (40 mL) was added quickly (in less than 1 minute) at this temperature with stirring. On completion of the fulvene addition the mixture was removed from the dry ice bath and warmed to room temperature, and a GC aliquot taken after ca. 15 minutes following removal of the dry-ice bath. The GC analysis indicated about 85.3% yield of the product had formed.

Stirring was continued for 7 hours, after which time the reaction mixture was quenched with a saturated NH$_4$Cl/H$_2$O solution (300 mL). The organic layer was extracted with diethyl ether, washed twice with H$_2$O (500 mL), dried over anhydrous Na$_2$SO$_4$, filtered, and the filtrate evaporated to dryness to afford a solid. Methanol (ca. 500 mL) was added to the solid and the mixture stirred overnight to afford the product as a finely divided white solid. After filtration, washing with MeOH, and drying overnight, 67 g (89%) of the desired parent ligand 1-(methyl)-1-(3-butenyl)-1-(cyclopentadienyl)-1-(2,7-di-tert-butylfluorenyl)methane was isolated and used without further purification.

Preparation 2. Following the same procedure as described in Preparation 1 above in a second preparation afforded 70 g (90%) of the desired compound.

Example 2

Comparative Preparation of 1-(methyl)-1-(3-butenyl)-1-(cyclopentadienyl)-1-(2,7-di-tert-butylfluorenyl)methane—Method A1

Preparation 1. A one-liter flask was charged with 2,7-di-tert-butylfluorene (50 g, 179.6 mmol) and a stir bar, capped with a rubber septum, and placed under a nitrogen atmosphere. Diethyl ether (about 300 mL) was added via a cannula, and the resulting mixture was cooled to –78° C. in a dry-ice bath. This mixture was stirred at this temperature as n-butyllithium (21.5 mL of 10 M in hexanes, 215 mmol) was added slowly via syringe. After the addition of n-butyllithium was complete, the reddish solution was slowly warmed to room temperature and stirred overnight (at least about 12 hours), to provide an ether solution of 2,7-di-tert-butylfluorenyl lithium.

Another one-liter flask fitted with an addition funnel was charged with 6-butenyl-6-methylfulvene (37 g, 253 mmol) and a stir bar, and cooled to 0° C. under a nitrogen atmosphere. The ether solution of 2,7-di-tert-butylfluorenyl lithium prepared as above was added in a dropwise fashion to the fulvene at 0° C. via the addition funnel over the course of approximately one hour. The resulting dark-colored reaction mixture was warmed to room temperature and stirred overnight (at least about 12 hours) under a nitrogen atmosphere. The reaction mixture was then quenched with the slow addition of a saturated NH$_4$Cl/H$_2$O solution (300 mL), the organic layer extracted with ether, washed twice with H$_2$O (500 mL), dried over anhydrous Na$_2$SO$_4$, filtered, and the filtrate evaporated to dryness. The crude product obtained by this method was then dissolved in pentane and maintained at about 0° C. in a freezer, thereby affording the product as a white solid that was washed with cold pentane, dried under vacuum, and isolated and used without further purification (60.4 g, 79%). Further product could be isolated in smaller quantities through concentrating the mother liquors and combined washings and placing them back in freezer.

Preparation 2. Another comparative preparation of the parent ligand 1-(methyl)-1-(3-butenyl)-1-(cyclopentadienyl)-1-(2,7-di-tert-butylfluorenyl)methane according to the same reaction, work-up, and crystallization conditions as disclosed in Method A1, afforded 34.7 g (45% yield) of the desired product as a white solid.

Example 3

Comparative Preparation of 1-(methyl)-1-(3-butenyl)-1-(cyclopentadienyl)-1-(2,7-di-tert-butylfluorenyl) methane—Method A2

An ether solution of 2,7-di-tert-butylfluorenyl lithium was prepared and added in a dropwise fashion over the course of approximately one hour to the neat 6-butenyl-6-methylfulvene (at 0° C.) in the same manner as disclosed in Method A1. The resulting reaction mixture was then warmed to room temperature and stirred for 2 days under a nitrogen atmosphere. After this time, an additional 5 mL of 6-butenyl-6-methylfulvene and an additional 30 mL of the n-butyllithium solution were added to the reaction mixture at room temperature and this mixture was stirred overnight at room temperature.

The reaction mixture was then quenched with the slow addition of a saturated NH$_4$Cl/H$_2$O solution (300 mL), the organic layer extracted with ether, washed twice with H$_2$O (500 mL), dried over anhydrous Na$_2$SO$_4$, filtered, and the filtrate evaporated to dryness. The crude product obtained by this method was dissolved in and crystallized from a pentane:Et$_2$O solution (4:1 mixture by volume) at about 0° C., thereby affording 50.1 g (66%) of the product as a white solid.

Example 4

Comparative Preparation of 1-(methyl)-1-(3-butenyl)-1-(cyclopentadienyl)-1-(2,7-di-tert-butylfluorenyl) methane—Method A3

A THF solution of 2,7-di-tert-butylfluorenyl lithium was prepared and added in a dropwise fashion over the course of approximately one hour to the 6-butenyl-6-methylfulvene solution (at 0° C.) in the same manner as disclosed in Method A1. The resulting dark-colored reaction mixture was then warmed to room temperature and stirred overnight (at least about 12 hours) under a nitrogen atmosphere. This THF reaction mixture was then quenched with the slow addition of a saturated $NH_4Cl/H_2O$ solution (300 mL), the organic layer extracted with diethyl ether, washed twice with $H_2O$ (500 mL), dried over anhydrous $Na_2SO_4$, filtered, and the filtrate evaporated to dryness. The crude product obtained by this method was then dissolved in and crystallized from pentane at about 0° C., thereby affording a 76% yield of the product as a white solid.

Example 5

Preparation of (5-cyclopentadienyl)[5-(2,7-di-tert-butylfluorenyl)]hex-1-ene zirconium dichloride The following preparations demonstrate that greater and more reproducible product yields of metallocene were improved under specific conditions which included selecting a length of time for the deprotonation reaction of the parent ligand with butyllithium, and removal of the reaction solvent (diethyl ether) prior to extraction of the product.

Preparation 1. A one-liter flask was charged with the parent ligand 1-(methyl)-1-(3-butenyl)-1-(cyclopentadienyl)-1-(2,7-di-tert-butylfluorenyl)methane (46.3 g, 109.0 mmol) and a stir bar, capped with a rubber septum, and placed under a nitrogen atmosphere. Diethyl ether (about 500 mL) was added to the flask and the mixture stirred and cooled to 0° C. in an ice bath. While stirring was continued, n-butyllithium (23 mL of 10 M in hexanes, 230 mmol) was added slowly to the mixture via syringe. After the addition of n-butyllithium was complete, the reaction mixture was warmed to room temperature and stirred overnight (at least about 12 hours) under a nitrogen atmosphere.

In a nitrogen-filled drybox, a one-liter flask was charged with $ZrCl_4$ (25.4 g, 109.0 mmol) and a stir bar, capped with a rubber septum, brought out of the drybox, charged with about 300 mL of pentane under nitrogen, and cooled in an ice bath to 0° C. The diethyl ether mixture of dilithiated parent ligand was added to the $ZrCl_4$ slurry via cannula over the course of thirty-minutes at 0° C., and the resulting orange slurry was warmed to room temperature and stirred overnight (at least about 12 hours). The solvent was then removed under vacuum affording an orange solid. Pentane (about 200 mL) was added to the solid, the slurry centrifuged and the supernatant decanted. The remaining solid was then extracted with methylene chloride, centrifuged, and the supernatant decanted and evaporated to dryness to afford 55.0 g (86%) of the desired metallocene (5-cyclopentadienyl)[5-(2,7-di-tert-butylfluorenyl)]hex-1-ene zirconium dichloride that was used without further purification.

Preparation 2. Duplication of the procedure used in Preparation 1 on two separate instances allowed isolation of the metallocene (5-cyclopentadienyl)[5-(2,7-di-tert-butylfluorenyl)]hex-1-ene zirconium dichloride in yields of 80% and 84% respectively.

Example 6

Comparative Preparation of (5-cyclopentadienyl)[5-(2,7-di-tert-butylfluorenyl)]hex-1-ene zirconium dichloride—Method B1

A one-liter flask was charged with the parent ligand 1-(methyl)-1-(3-butenyl)-1-(cyclopentadienyl)-1-(2,7-di-tert-butylfluorenyl)methane (23.2 g, 54.6 mmol) and a stir bar, capped with a rubber septum, and placed under a nitrogen atmosphere. Diethyl ether (about 300 mL) was added to the flask and the mixture stirred and cooled to −78° C. in a dry ice bath. While stirring was continued, n-butyllithium (12 mL of 10 M in hexanes, 120 mmol) was added slowly to the mixture via syringe. After the addition of n-butyllithium was complete, the reaction mixture was warmed to room temperature and stirred for 6 hours while under a nitrogen atmosphere.

In a nitrogen-filled drybox, a one-liter flask was charged with $ZrCl_4$ (12.7 g, 54.5 mmol) and a stir bar, capped with a rubber septum, brought out of the drybox, charged with about 500 mL of pentane under nitrogen, cooled in an ice bath to 0° C., and fitted with an addition funnel. The diethyl ether mixture of dilithiated parent ligand was added to the $ZrCl_4$ slurry via the addition funnel over the course of one hour at 0° C., and the resulting orange slurry was warmed to room temperature and stirred overnight (at least about 12 hours). The resulting slurry was then centrifuged and the supernatant decanted and evacuated to dryness to afford 16 g of solid. The residual solid was then extracted with anhydrous and oxygen-free methylene chloride, centrifuged, and the supernatant decanted and evaporated to dryness to afford 13.6 g (43%) of the desired metallocene (5-cyclopentadienyl)[5-(2,7-di-tert-butylfluorenyl)]hex-1-ene zirconium dichloride that was used without further purification.

Example 7

Comparative One-Pot Preparation of (5-cyclopentadienyl)[5-(2,7-di-tert-butylfluorenyl)]hex-1-ene zirconium dichloride—Method C An aliquot of n-butyl lithium (9.3 mL, 2.5 M in hexanes, 23.3 mmol) was added dropwise to 2,7-di-t-butylfluorene (5.85 g, 21 mmol) dissolved in $Et_2O$ (40 mL) at 0° C. The resulting mixture was warmed to room temperature and stirred for an additional 3 hours, giving rise to a dark red solution (lithium 2,7-di-t-butylfluorenyl, abbreviated t-BuFluLi). This solution was added dropwise to a solution of 6-butenyl-6-methylfulvene (3.4 g, 23.1 mmol) in 10 mL of $Et_2O$ at 0° C. over a period of 30 minutes. The resulting mixture was stirred at room temperature overnight (at least about 12 hours), giving rise to a dark red solution. An additional amount of fulvene (0.9 g, 6.2 mmol) was then added to this solution at room temperature and the resulting mixture was stirred for an additional 4 hours to provide a dark red solution. A portion of n-butyl lithium (9.3 mL, 2.5 M in hexanes, 23.3 mmol) was added dropwise to this solution at 0° C., after which the resulting mixture was warmed to room temperature and stirred for an additional 3 hours to provide a dark red solution of the dilithiated parent ligand (dilithiated 1-(methyl)-1-(3-butenyl)-1-(cyclopentadienyl)-1-(2,7-di-tert-butylfluorenyl)methane). This solution was then added dropwise to $ZrCl_4$ (5.38 g, 23.1 mmol) suspended in $Et_2O$ (50 mL) at 0° C. over a period of 20 minutes. The resulting mixture was warmed to room temperature and stirred overnight, giving rise to an orange-brown slurry. The slurry was centrifuged and the supernatant decanted and evaporated to dryness to give about 10 g of a dark brown solid. The remaining solid was extracted with CH$_2$Cl$_2$ (ca. 180 mL) and the extract evaporated to dryness to give the metallocene (5-cyclopentadienyl)[5-(2,7-di-tert-butylfluorenyl)]-hex-1-ene zirconium dichloride as an orange red solid (3.5 g, 28.5% yield) that could be used without further purification.

Although any methods, devices, and materials similar to or equivalent to those described herein can be used in the practice or testing of the invention, the typical methods, devices and materials are herein described.

All publications and patents mentioned herein are incorporated herein by reference in their entireties, for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

To the extent that any definition or usage provided by any document incorporated herein by reference conflicts with the definition or usage provided herein, the definition or usage provided herein controls.

We claim:

1. A method of making a compound of the formula

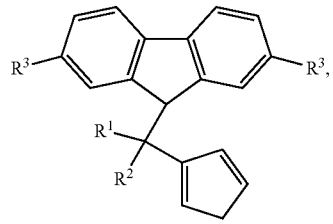

(I)

and isomers thereof, comprising:
a) contacting a compound of the formula

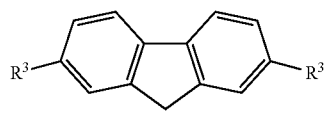

(II)

and an alkyl lithium reagent in an ethereal solvent to form a first mixture, wherein the compound of the formula II is substantially deprotonated to form a lithium salt of compound II, Li(II);
b) rapidly combining the first mixture with a fulvene compound of the formula

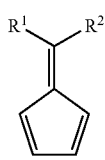

(III)

to form a second mixture, wherein either the lithium salt of compound II, Li(II), or the compound of the formula III is optionally a limiting reagent, and wherein the limiting reagent, if present, has substantially reacted; and
c) contacting the second mixture with a proton source to form a third mixture comprising

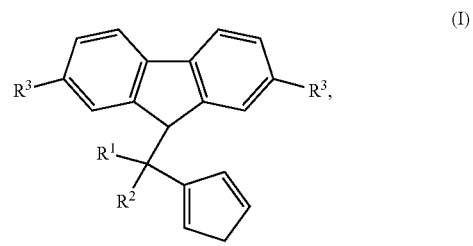

(I)

and isomers thereof;
wherein R$^1$ and R$^2$ independently are hydrogen or an aliphatic or substituted aliphatic group having from 1 to about 20 carbon atoms; and
wherein each R$^3$ independently is hydrogen or an aliphatic or substituted aliphatic group having from 1 to about 20 carbon atoms.

2. The method of claim 1, wherein: compound I has the formula

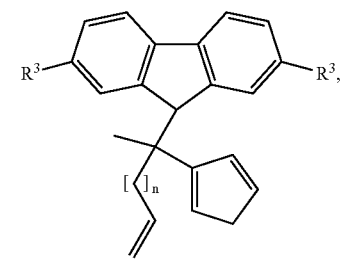

compound II has the formula

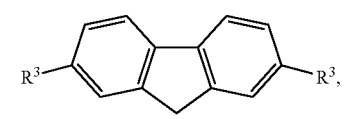

and compound III has the formula

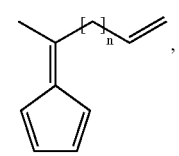

wherein:
R$^3$ is H, t-butyl, i-propyl, n-propyl, ethyl, or methyl, and n is an integer from 1 to about 6.

3. The method of claim 1, further comprising isolating the compound of the formula I.

4. The method of claim 1, further comprising removing the volatile components from the third mixture to provide a residue comprising the compound of the formula I.

5. The method of claim 1, further comprising removing the volatile components from the third mixture to provide a residue comprising the compound of the formula I, optionally triturating the residue with a solvent in which the compound of the formula I is substantially insoluble and the compound of the formula III is soluble, and isolating the compound of the formula I.

6. The method of claim 5, wherein the compound of the formula I is isolated in at least about 85% yield.

7. The method of claim 5, wherein the trituration solvent comprises an alcohol.

8. The method of claim 5, wherein the trituration solvent comprises methanol, ethanol, i-propanol, n-propanol, n-butanol, sec-butanol, t-butanol, 1-hexanol, 2-hexanol, 3-hexanol, any mixture thereof, or any combination thereof.

9. The method of claim 5, wherein the trituration solvent comprises methanol, ethanol, any mixture thereof, or any combination thereof.

10. The method of claim 1, wherein the ethereal solvent comprises dimethyl ether, diethyl ether, diisopropyl ether, di-n-propyl ether, di-n-butyl ether, methyl t-butyl ether, diphenyl ether, THF, 1,2-dimethoxyethane, or any combination thereof.

11. The method of claim 1, wherein the ethereal solvent comprises diethyl ether, THF, or any combination thereof.

12. The method of claim 1, wherein the ethereal solvent comprises diethyl ether.

13. The method of claim 1, wherein the concentration of the lithium salt of compound II, Li(II), reagent in the first mixture prior to rapidly combining the first mixture with the compound of the formula III, is from about 0.5 M to about 1.8 M.

14. The method of claim 1, wherein the concentration of the lithium salt of compound II, Li(II), reagent in the first mixture prior to rapidly combining the first mixture with the compound of the formula III, is from about 0.7 M to about 1.5 M.

15. The method of claim 1, wherein the alkyl lithium reagent comprises MeLi, n-BuLi, t-BuLi, n-hexylLi, LiCH$_2$SiMe$_3$, LiCH$_2$Ph, LiCH$_2$CMe$_3$, or any combination thereof.

16. The method of claim 1, wherein the compound of the formula II and the alkyl lithium reagent react to form the lithium salt of compound II, Li(II), in at least about 95% yield.

17. The method of claim 1, wherein the first mixture is combined with the compound of the formula III over a time period of less than about 3 minutes.

18. The method of claim 1, wherein the first mixture is combined with the compound of the formula III over a time period of less than about 1 minute.

19. The method of claim 1, wherein the first mixture is combined with the compound of the formula III over a time period of less than about 30 seconds.

20. The method of claim 1, wherein the proton source comprises water, an aqueous acid, an aqueous ammonium salt, or any combination thereof.

21. The method of claim 1, wherein step a is initiated from about 0° C. to about −100° C.

22. The method of claim 1, wherein step a is initiated at about −78° C.

23. The method of claim 1, wherein step a is conducted from about room temperature to about −78° C.

24. The method of claim 1, wherein step b is initiated from about 0° C. to about −100° C.

25. The method of claim 1, wherein step b is initiated at about −78° C.

26. The method of claim 1, wherein step b is conducted from about room temperature to about −78° C.

27. The method of claim 1, wherein the limiting reagent of step b is present in at least about 50% the mole fraction of the non-limiting reagent.

28. The method of claim 1, wherein at least about 90% of the limiting reagent of step b has reacted.

29. The method of claim 1, wherein at least about 95% of the limiting reagent of step b has reacted.

30. The method of claim 1, wherein the compound of the formula I is formed in at least about 85% yield.

31. The method of claim 1, wherein the compound of the formula I is formed in at least about 90% yield.

32. The method of claim 1, wherein the compound of the formula I is formed in at least about 95% yield.

33. A method for making (5-cyclopentadienyl)[5-(2,7-di-tert-butylfluorenyl)]hex-1-ene, comprising:
   a) contacting 2,7-di-tert-butylfluorene and an alkyl lithium reagent in an ethereal solvent to form a first mixture, wherein the 2,7-di-tert-butylfluorene is substantially deprotonated to form Li(2,7-di-tert-butylfluorenyl);
   b) rapidly combining the ethereal solution of Li(2,7-di-tert-butylfluorenyl) with 6-methyl-6-(3-butenyl)fulvene,

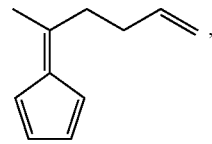

to form a second mixture, wherein the limiting reagent has substantially reacted; and
   c) contacting the second mixture with a proton source to form a third mixture comprising (5-cyclopentadienyl)[5-(2,7-di-tert-butylfluorenyl)]hex-1-ene in at least about 85% yield.

34. The method of claim 33, further comprising isolating the (5-cyclopentadienyl)[5-(2,7-di-tert-butylfluorenyl)]hex-1-ene.

35. The method of claim 33, further comprising removing the volatile components from the third mixture to provide a residue comprising (5-cyclopentadienyl)[5-(2,7-di-tert-butylfluorenyl)]hex-1-ene.

36. The method of claim 33, further comprising removing the volatile components from the third mixture to provide a residue comprising (5-cyclopentadienyl)[5-(2,7-di-tert-butylfluorenyl)]hex-1-ene, optionally triturating the residue with a solvent in which (5-cyclopentadienyl)[5-(2,7-di-tert-butylfluorenyl)]hex-1-ene is substantially insoluble and 6-methyl-6-(3-butenyl)fulvene is soluble, and isolating the (5-cyclopentadienyl)[5-(2,7-di-tert-butylfluorenyl)]hex-1-ene.

37. The method of claim 33, wherein (5-cyclopentadienyl)[5-(2,7-di-tert-butylfluorenyl)]hex-1-ene is isolated in at least about 85% yield.

38. The method of claim 33, wherein the trituration solvent is an alcohol.

39. The method of claim 33, wherein the trituration solvent comprises methanol, ethanol, i-propanol, n-propanol, n-butanol, sec-butanol, t-butanol, 1-hexanol, 2-hexanol, 3-hexanol, any mixture thereof, or any combination thereof.

40. The method of claim 33, wherein the ethereal solvent comprises dimethyl ether, diethyl ether, diisopropyl ether, di-n-propyl ether, di-n-butyl ether, methyl t-butyl ether, diphenyl ether, THF, 1,2-dimethoxyethane, or any combination thereof.

41. The method of claim 33, wherein the alkyl lithium reagent comprises MeLi, n-BuLi, t-BuLi, n-hexylLi, $LiCH_2SiMe_3$, $LiCH_2Ph$, $LiCH_2CMe_3$, or any combination thereof.

42. The method of claim 33, wherein the ethereal solution of Li(2,7-di-tert-butylfluorenyl) is combined with 6-methyl-6-(3-butenyl)fulvene over a time period of less than about 3 minutes.

43. The method of claim 33, wherein the ethereal solution of Li(2,7-di-tert-butylfluorenyl) is combined with 6-methyl-6-(3-butenyl)fulvene over a time period of less than about 1 minute.

44. The method of claim 33, wherein the ethereal solution of Li(2,7-di-tert-butylfluorenyl) is combined with 6-methyl-6-(3-butenyl)fulvene over a time period of less than about 30 seconds.

45. The method of claim 33, wherein the proton source comprises water, an aqueous acid, an aqueous ammonium salt, or any combination thereof.

46. A method for making a compound of the formula

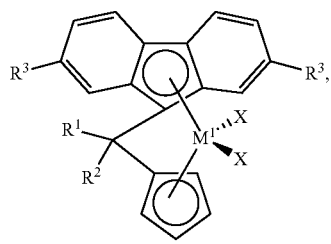

(IV)

comprising:

a) contacting a compound of the formula

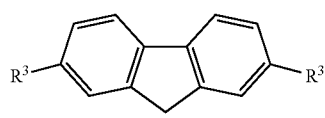

(II)

and a first alkyl lithium reagent in a first ethereal solvent to form a first mixture, wherein the compound of the formula II is substantially deprotonated to form a lithium salt of compound II, Li(II);

b) rapidly combining the first mixture with a fulvene compound of the formula

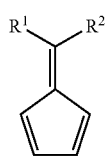

(III)

to form a second mixture, wherein the limiting reagent has substantially reacted;

c) contacting the second mixture with a proton source to form a third mixture comprising

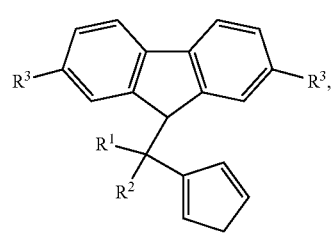

(I)

including isomers thereof, in at least about 85% yield;

d) removing the volatile components from the third mixture to provide a residue comprising the compound of the formula I;

e) optionally triturating the residue with a solvent in which the compound of the formula I is substantially insoluble and the compound of the formula III is soluble to provide the compound of the formula I, followed by isolation of the compound of the formula I;

f) contacting the compound of the formula I with from about 2 to about 2.5 molar equivalents of a second alkyl lithium reagent in a second ethereal solvent to form a fourth mixture, wherein the compound of the formula I is substantially deprotonated to form a dilithium salt of compound I, $Li_2(I)$;

g) contacting the fourth mixture with $M^1X_4$ and an optional hydrocarbon cosolvent to form a fifth mixture comprising

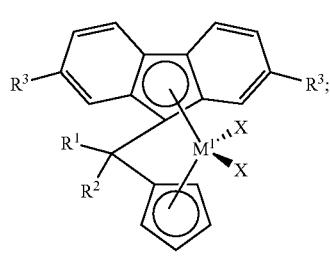

(IV)

h) removing the volatile components from the fifth mixture to provide the compound of the formula IV in at least about 80% yield;

i) optionally washing the compound of the formula IV in a non-polar solvent;

j) optionally extracting the compound of the formula IV with a polar solvent followed by removing the volatiles from the polar solvent solution to provide the compound of the formula IV; and k) optionally crystallizing the compound of the formula IV from an aromatic solvent; wherein:

$R^1$ and $R^2$ are independently selected from an aliphatic or substituted aliphatic group having from 1 to about 20 carbon atoms, or hydrogen; and $R^3$, in each instance, is independently selected from an aliphatic or substituted aliphatic group having from 1 to about 20 carbon atoms, or hydrogen;

$M^1$ is Zr or Hf; and

X is Cl, Br, or I.

47. The method of claim 46, wherein: compound I has the formula

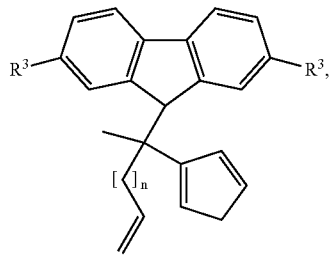

compound II has the formula

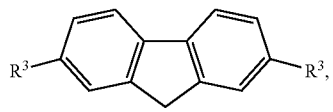

and compound III has the formula

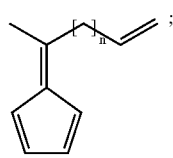

wherein:
R³ is H, t-butyl, i-propyl, n-propyl, ethyl, or methyl,
n is an integer from 1 to about 6;
M¹ is Zr; and
X is Cl.

48. The method of claim 46, wherein the optional trituration solvent is an alcohol.

49. The method of claim 46, wherein the first and second alkyl lithium reagents independently comprise MeLi, n-BuLi, t-BuLi, n-hexylLi, LiCH₂SiMe₃, LiCH₂Ph, LiCH₂CMe₃, or any combination thereof.

50. The method of claim 46, wherein the first and second ethereal solvents independently comprise dimethyl ether, diethyl ether, diisopropyl ether, di-n-propyl ether, di-n-butyl ether, methyl t-butyl ether, diphenyl ether, THF, 1,2-dimethoxyethane, or any combination thereof.

51. The method of claim 46, wherein the fourth mixture comprises the dilithium salt of compound I, Li₂(I) in at least about 90% yield.

52. The method of claim 46, wherein the hydrocarbon cosolvent comprises butane, pentane, cyclopentane, hexane, heptane, cyclohexane, methyl cyclopentane, octane, or any combination thereof.

53. The method of claim 46, wherein the non-polar solvent comprises butane, pentane, cyclopentane, hexane, heptane, cyclohexane, methyl cyclopentane, octane, or any combination thereof.

54. The method of claim 46, wherein the polar solvent comprises CHCl₃, CH₂Cl₂, 1,2-dichlorethane, or any combination thereof.

55. The method of claim 46, wherein the aromatic solvent comprises benzene, toluene, xylene, mesitylene, ethyl benzene, anisole, aniline, or any combination thereof.

56. The method of claim 46, wherein the compound of the formula II and the first alkyl lithium reagent react to form the lithium salt of compound II, Li(II), in at least about 95% yield.

57. The method of claim 46, wherein the first mixture is combined with the compound of the formula III over a time period of less than about 3 minutes.

58. The method of claim 46, wherein the first mixture is combined with the compound of the formula III over a time period of less than about 1 minute.

59. The method of claim 46, wherein the first mixture is combined with the compound of the formula III over a time period of less than about 30 seconds.

60. A method for isolating (5-cyclopentadienyl)[5-(2,7-di-tert-butylfluorenyl)]hex-1-ene zirconium dichloride, comprising:
a) contacting 2,7-di-tert-butylfluorene and a first alkyl lithium reagent in a first ethereal solvent to form a first mixture, wherein the 2,7-di-tert-butylfluorene is substantially deprotonated to form Li(2,7-di-tert-butylfluorenyl);
b) rapidly combining the first ethereal solution of Li(2,7-di-tert-butylfluorenyl) with 6-methyl-6-(3-butenyl)fulvene,

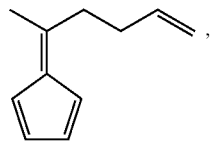

to form a second mixture, wherein the limiting reagent has substantially reacted;
c) contacting the second mixture with a proton source to form a third mixture comprising (5-cyclopentadienyl)[5-(2,7-di-tert-butylfluorenyl)]hex-1-ene in at least about 85% yield;
d) removing the volatile components from the third mixture to provide a residue comprising (5-cyclopentadienyl)[5-(2,7-di-tert-butylfluorenyl)]hex-1-ene;
e) optionally triturating the residue with a solvent in which (5-cyclopentadienyl)[5-(2,7-di-tert-butylfluorenyl)]hex-1-ene is substantially insoluble and 6-methyl-6-(3-butenyl)fulvene is soluble, and isolating the (5-cyclopentadienyl)[5-(2,7-di-tert-butylfluorenyl)]hex-1-ene;
f) contacting the (5-cyclopentadienyl)[5-(2,7-di-tert-butylfluorenyl)]hex-1-ene with from about 2 to about 2.5 molar equivalents of a second alkyl lithium reagent in a second ethereal solvent to form a fourth mixture, wherein the (5-cyclopentadienyl)[5-(2,7-di-tert-butylfluorenyl)]hex-1-ene is substantially deprotonated to form Li₂(5-cyclopentadienyl)[5-(2,7-di-tert-butylfluorenyl)]hex-1-ene;
g) contacting the fourth mixture with ZrCl₄ and an optional hydrocarbon cosolvent to form a fifth mixture comprising (5-cyclopentadienyl)[5-(2,7-di-tert-butylfluorenyl)]hex-1-ene zirconium dichloride;
h) removing the volatile components from the fifth mixture to provide (5-cyclopentadienyl)[5-(2,7-di-tert-butylfluorenyl)]hex-1-ene zirconium dichloride in at least about 80% yield;
i) optionally washing the (5-cyclopentadienyl)[5-(2,7-di-tert-butylfluorenyl)]hex-1-ene zirconium dichloride in a non-polar solvent;

j) optionally extracting the (5-cyclopentadienyl)[5-(2,7-di-tert-butylfluorenyl)]hex-1-ene zirconium dichloride with a polar solvent followed by removing the volatiles from the polar solvent solution to provide (5-cyclopentadienyl)[5-(2,7-di-tert-butylfluorenyl)]hex-1-ene zirconium dichloride; and k) optionally crystallizing the (5-cyclopentadienyl)[5-(2,7-di-tert-butylfluorenyl)]hex-1-ene zirconium dichloride from an aromatic solvent.

61. The method of claim 60, wherein the first ethereal solution of Li(2,7-di-tert-butylfluorenyl) is combined with 6-methyl-6-(3-butenyl)fulvene over a time period of less than about 3 minutes.

62. The method of claim 60, wherein the ethereal solution of Li(2,7-di-tert-butylfluorenyl) is combined with 6-methyl-6-(3-butenyl)fulvene over a time period of less than about 1 minute.

63. The method of claim 60, wherein the ethereal solution of Li(2,7-di-tert-butylfluorenyl) is combined with 6-methyl-6-(3-butenyl)fulvene over a time period of less than about 30 seconds.

64. A method of making a compound of the formula

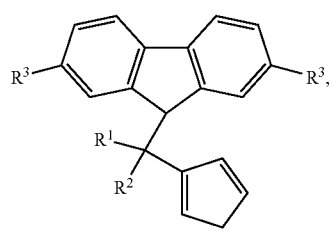

(I)

and isomers thereof, comprising:

a) providing a source of a fluorenyl anion having the formula

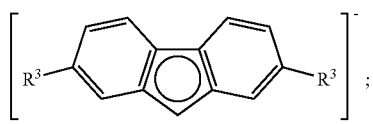

b) rapidly combining the source of the fluorenyl anion with a fulvene compound of the formula

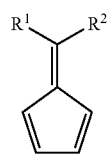

(III)

to form a mixture, wherein either the source of the fluorenyl anion or the compound of the formula III is optionally a limiting reagent, and wherein the limiting reagent, if present, has substantially reacted; and

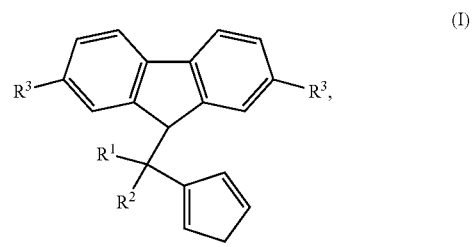

(I)

c) contacting the mixture with a proton source to form and isomers thereof;

wherein $R^1$ and $R^2$ independently are hydrogen or an aliphatic or substituted aliphatic group having from 1 to about 20 carbon atoms; and wherein each $R^3$ independently is hydrogen or an aliphatic or substituted aliphatic group having from 1 to about 20 carbon atoms.

65. The method of claim 64, wherein the source of a fluorenyl anion is a compound comprising lithium, sodium, potassium, magnesium, calcium, or a combination thereof.

66. A method of making a compound of the formula

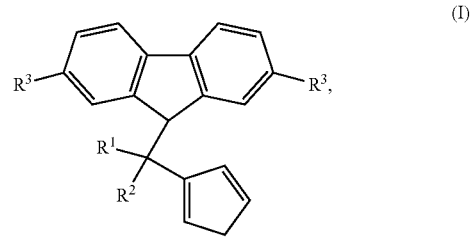

(I)

and isomers thereof, comprising:

a) providing a salt of a fluorenyl anion having the formula

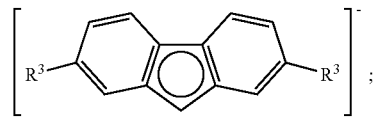

b) rapidly combining the source of the fluorenyl anion with a fulvene compound of the formula

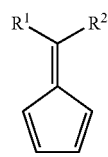

(III)

to form a mixture, wherein either the source of the fluorenyl anion or the compound of the formula III is optionally a limiting reagent, and wherein the limiting reagent, if present, has substantially reacted; and

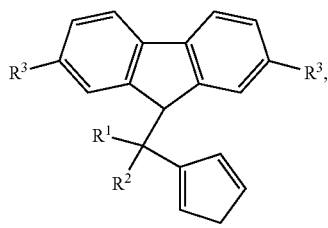
(I)

c) contacting the mixture with a proton source to form and isomers thereof;
wherein $R^1$ and $R^2$ independently are hydrogen or an aliphatic or substituted aliphatic group having from 1 to about 20 carbon atoms; and
wherein each $R^3$ independently is hydrogen or an aliphatic or substituted aliphatic group having from 1 to about 20 carbon atoms.

67. The method of claim 66, wherein the salt of a fluorenyl anion is a compound comprising lithium, sodium, potassium, magnesium, calcium, or a combination thereof.

* * * * *